US012649046B2

(12) United States Patent
Wang et al.

(10) Patent No.: US 12,649,046 B2
(45) Date of Patent: Jun. 9, 2026

(54) SHEATH

(71) Applicant: LIFETECH SCIENTIFIC (SHENZHEN) CO., LTD., Shenzhen (CN)

(72) Inventors: Gang Wang, Shenzhen (CN); Feng Peng, Shenzhen (CN); Wei Jiang, Shenzhen (CN); Quanyuan Wang, Shenzhen (CN)

(73) Assignee: LIFETECH SCIENTIFIC (SHENZHEN) CO., LTD., Shenzhen (CN)

(*) Notice: Subject to any disclaimer, the term of this patent is extended or adjusted under 35 U.S.C. 154(b) by 1086 days.

(21) Appl. No.: 17/770,367

(22) PCT Filed: Oct. 26, 2020

(86) PCT No.: PCT/CN2020/123758
§ 371 (c)(1),
(2) Date: Apr. 20, 2022

(87) PCT Pub. No.: WO2021/120853
PCT Pub. Date: Jun. 24, 2021

(65) Prior Publication Data
US 2022/0387757 A1      Dec. 8, 2022

(30) Foreign Application Priority Data

Dec. 17, 2019    (CN) .......................... 201911300556.1
Dec. 17, 2019    (CN) .......................... 201911301111.5
(Continued)

(51) Int. Cl.
A61M 25/01        (2006.01)
A61B 17/00        (2006.01)
A61M 25/06        (2006.01)

(52) U.S. Cl.
CPC ... A61M 25/0147 (2013.01); A61B 17/00234 (2013.01); A61M 25/0136 (2013.01);
(Continued)

(58) Field of Classification Search
CPC ...................... A61M 2025/015; A61B 1/0057
(Continued)

(56) References Cited

U.S. PATENT DOCUMENTS 4,895,346 A        1/1990  Steigerwald
2002/0128604 A1    9/2002  Nakajima
(Continued)

FOREIGN PATENT DOCUMENTS

CN        102580225 A        7/2012
CN        103877663 A        6/2014
(Continued)

OTHER PUBLICATIONS

Partial Search Report issued on Dec. 19, 2023, in corresponding European Application No. 20902663.2, 17 pages.
(Continued)

*Primary Examiner* — Jason E Flick
*Assistant Examiner* — Isabella S North
(74) *Attorney, Agent, or Firm* — Maier & Maier, PLLC

(57)        ABSTRACT

A sheath, including a sheath body, a handle, and a traction wire. The traction wire includes a first traction wire. The handle includes a first guide rail member and a first slider. The first slider is connected to the first traction wire. A first groove is provided on an outer wall of the first guide rail member along an axial direction. The first groove includes a first bottom and a first side wall. The first slider slides in the first groove along the first side wall so as to drive the first traction wire to move. At least part of the outer wall of the
(Continued)

first guide rail member is radially recessed to a central shaft of the first guide rail member to form the first groove.

8 Claims, 9 Drawing Sheets

(30) Foreign Application Priority Data

Dec. 17, 2019   (CN) .......................... 201922271986.7
Dec. 24, 2019   (CN) .......................... 201911351255.1

(52) U.S. Cl.
    CPC .................... *A61M 25/0662* (2013.01); *A61B 2017/00323* (2013.01); *A61M 2025/015* (2013.01)

(58) Field of Classification Search
    USPC ...................................................... 604/95.04
    See application file for complete search history.

(56) References Cited

U.S. PATENT DOCUMENTS

| | | | |
|---|---|---|---|
| 2008/0139999 A1 | 6/2008 | Gibson et al. | |
| 2011/0282176 A1* | 11/2011 | Tegg ................. | A61M 25/0136 |
| | | | 604/95.04 |
| 2011/0282286 A1 | 11/2011 | Argentine | |
| 2015/0231366 A1* | 8/2015 | Davies .............. | A61M 25/0136 |
| | | | 604/95.04 |
| 2015/0246205 A1 | 9/2015 | Schaeffer | |
| 2016/0367787 A1* | 12/2016 | Van Hoven ............. | A61F 2/246 |
| 2019/0254504 A1 | 8/2019 | Ide | |

FOREIGN PATENT DOCUMENTS

| | | | | |
|---|---|---|---|---|
| CN | 106419990 | A | 2/2017 | |
| CN | 107174724 | A | 9/2017 | |
| CN | 109223064 | A | 1/2019 | |
| CN | 110037760 | A | 7/2019 | |
| CN | 110215241 | A | 9/2019 | |
| CN | 110215593 | A | 9/2019 | |
| CN | 211935126 | U | 11/2020 | |
| CN | 112971870 | A | 6/2021 | |
| CN | 112971871 | A | 6/2021 | |
| WO | 2010141837 | A1 | 12/2010 | |
| WO | WO-2019180268 | A1 * | 9/2019 | ........ A61M 25/0147 |

OTHER PUBLICATIONS

Office Action issued on Oct. 11, 2021, in connection with corresponding Chinese Application No. 201911300556.1 (17 pp., including machine-generated English translation).

Office Action issued on May 26, 2022, in connection with corresponding Chinese Application No. 201911300556.1 (16 pp., including machine-generated English translation).

Office Action issued on Oct. 11, 2021, in connection with corresponding Chinese Application No. 201911301111.5 (17 pp., including machine-generated English translation).

Office Action issued on May 25, 2022, in connection with corresponding Chinese Application No. 201911301111.5 (16 pp., including machine-generated English translation).

Office Action issued on Oct. 26, 2021, in connection with corresponding Chinese Application No. 201911351255.1 (15 pp., including machine-generated English translation).

Office Action issued on Aug. 3, 2022, in connection with corresponding Chinese Application No. 201911351255.1 (12 pp., including machine-generated English translation).

Office Action issued on Oct. 17, 2024, in corresponding Chinese Application No. 202211311640.5, 12 pages, with Partial English Translation.

Office Action issued on Oct. 21, 2024, in corresponding Chinese Application No. 202211311249.5, 9 pages, with Partial English Translation.

International Search Report mailed Feb. 1, 2021, in corresponding to International Application No. PCT/CN2020/123758; 9 pages (with English Translation).

Office Action issued on Sep. 5, 2022, in corresponding Chinese Application No. 201911300556.1, 13 pages.

Office Action issued on Oct. 21, 2022, in corresponding India Application No. 202217032437, 6 pages.

\* cited by examiner

A–A

340

SHEATH

TECHNICAL FIELD

The present invention relates to the field of medical devices, in particular to a sheath.

BACKGROUND

Medical sheaths have been widely used in minimally invasive interventional diagnosis and treatment operations to establish channels, transport or withdraw instruments, import drugs, or export body fluids. A bendable sheath has a distal-end bending function, so that it can quickly and reliably reach a target lesion position to reduce the operation time.

An existing bendable sheath for conveying medical devices in the market has a mono-bendable distal sheath head. The position of the distal sheath head can be adjusted through the free bending of the distal end, but the angle cannot be adjusted accurately, and the operation is complicated and laborious.

Human anatomical structures are quite different. The sheath with the mono-bendable distal curved sheath head is used for conveying a device, which cannot completely solve specific cases and easily causes that a medical device fails in reaching the target lesion position or that the medical device reaches the target lesion position, but release fails, and the device falls off, which causes a great bodily harm to a patient.

In the process of establishing an access for interventional devices by the existing conveying sheath during an operation, due to its poor sealing effect, blood leakage is likely to occur, which is not convenient for doctors to operate, is not conducive to the safety of the operation, and cannot effectively meet the needs of clinical use.

SUMMARY

Based on this, it is desired to provide a sheath, including a sheath body, a handle, and a traction wire. A proximal end of the sheath body is connected to the handle; the traction wire is connected to the sheath body and the handle and includes a first traction wire; the handle includes a first guide rail member and a first slider; the first slider is connected to the first traction wire; a first groove is provided on an outer wall of the first guide rail member along an axial direction; the first groove includes a first bottom and a first side wall; the first slider slides in the first groove along the first side wall so as to drive the first traction wire to move; at least part of the outer wall of the first guide rail member is radially recessed to a center axis of the first guide rail member to form the first groove; alternatively, the first bottom of the first groove is at least part of an outer surface of the first guide rail member, and the first side wall is located on the outer surface of the first guide rail member.

According to the above-mentioned sheath, the outer wall of the first guide rail member is provided with the first groove along the axial direction, and the first slider is arranged in the first groove, so that the whole device is simple and compact in design. The first slider is connected to the first traction wire, and the first slider slides in the first groove to drive the first traction wire to move, which can easily control a sliding distance of the first slider, so that a bending angle of the sheath body can be accurately controlled, and the operation is more convenient.

A sheath includes a sheath body, a handle, and a traction wire; a proximal end of the sheath body is connected to the handle; the traction wire is connected to the sheath body and the handle;

the handle includes a first guide rail member, a second guide rail member, a first slider, and a second slider; a distal end of the first guide rail member and a proximal end of the second guide rail member are oppositely disposed; a proximal end of the sheath body passes through any one of the first guide rail member and the second guide rail member in sequence and then passes through the other one of the first guide rail member and the second guide rail member; the first slider does a reciprocating movement on the first guide rail member; the second slider does a reciprocating movement on the second guide rail member;

the sheath body includes a first section, a second section, and a third section; two ends of the third section are respectively connected to the first section and the second section; the hardness of the third section is greater than that of the first section and that of the second section;

the traction wire includes a first traction wire and a second traction wire; the first traction wire is connected to the first section and the first slider; the second traction wire is connected to the second section and the second slider; the reciprocating movement of the first slider drives the first section to bend and do a straightening movement; and the reciprocating movement of the second slider drives the second section to bend and do a straightening movement.

According to the above-mentioned sheath, the first guide rail member, the first slider, and the first traction wire cooperate with each other, and the second guide rail member, the second slider, and the second traction wire cooperate with each other, thereby controlling at least two positions on the sheath body portion of the bendable sheath to bend; the proximal end of the sheath body passes through any one of the first guide rail member and the second guide rail member in sequence and then passes through the other one of the first guide rail member and the second guide rail member, so that the whole device is more compact; the two ends of the third section are respectively connected to the first section and the second section, and the hardness of the third section is greater than that of the first section and that of the second section, so that the first section and the second section will not interfere with each other in a bending process, and accurate control and release can be achieved.

DETAILED DESCRIPTION OF THE EMBODIMENTS

In order to make the foregoing objectives, features and advantages of the embodiments more clear and understandable, the implementation modes of the embodiments are described in detail with reference to the accompanying drawings. Many details are described in the following descriptions to facilitate full understanding of the embodiments. However, the embodiments can be implemented in a variety of other ways than those described herein, and those skilled in the art can make similar improvements without departing from the scope of the embodiments. Therefore, the embodiments are not limited by implementations of the embodiments.

Unless otherwise defined, all technical and scientific terms used herein are the same as meanings of general understandings of those skilled in the art of the embodiments. The terms used in the description herein are merely to describe the embodiments, are and not intending as limiting.

First, a "proximal end" mentioned in the embodiments refers to an end close to an operator during operation; a "distal end" refers to an end far away from the operator during operation; "axial" refers to a direction parallel to a connecting line between a center of a distal end and a center of a proximal end of a medical apparatus; and "radial" refers to a direction perpendicular to an axial direction.

Figure 1:
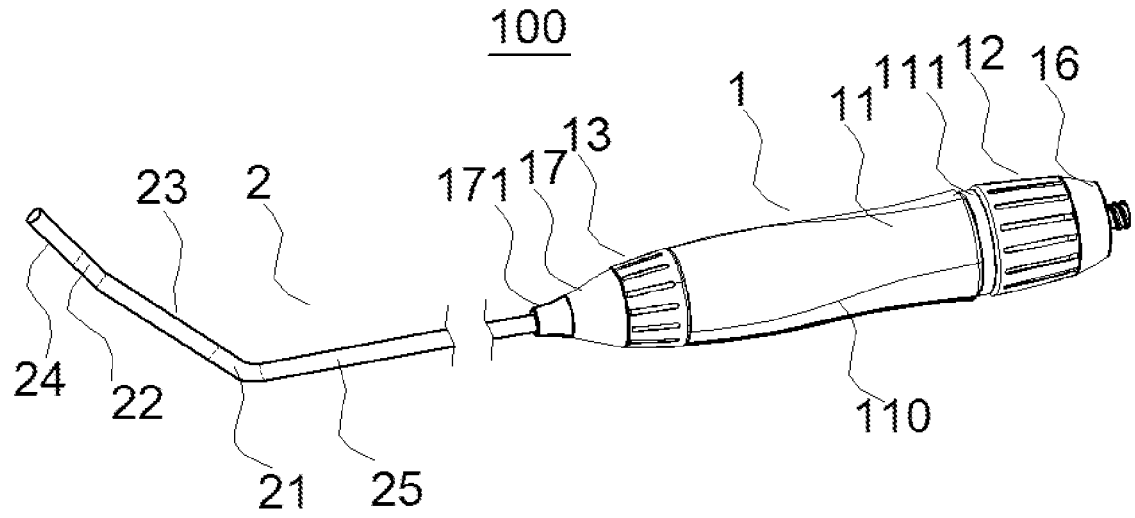
FIG. 1 is a schematic diagram of a bendable sheath provided by one embodiment.

Referring to FIG. 1, this embodiment provides a bendable sheath 100, including a handle 1 and a sheath body 2. A proximal end of the sheath body 2 is connected to the handle 1. In this embodiment, the bendable sheath 100 is a dual-bendable sheath, that is, the sheath body 2 includes two bendable positions.

In terms of the appearance, the handle 1 includes a housing 11, a first curvature adjustment knob 12, a second curvature adjustment knob 13, a front end cover 17, and a rear end cover 16. The housing 11 is arranged between the first curvature adjustment knob 12 and the second curvature adjustment knob 13. A distal end of the first curvature adjustment knob 12 resists against a proximal end of the housing 11, and a proximal end of the first curvature adjustment knob 12 resists against the rear end cover 16. A proximal end of the second curvature adjustment knob 13 resists against a distal end of the housing 11, and a distal end of the second curvature adjustment knob 13 resists against the front end cover 17.

A distal end of the front end cover 17 is connected with a horn-type protective sleeve 171. A material of the protective sleeve 171 is silica gel or rubber. The proximal end of the sheath body 2 threaded in from a proximal end of the protective sleeve 171. The protective sleeve 171 is used for avoiding breakage caused by an extremely large bending angle of part of the sheath body 2 that is in contact with the protective sleeve 171.

In this embodiment, the first curvature adjustment knob 12 and the second curvature adjustment knob 13 rotate respectively with respect to the housing 11. An operator can hold the housing 11 with a hand and grasp the first curvature adjustment knob 12 or the second curvature adjustment knob 13 directly with the thumb and the index finger to rotate them, thus making the operation more convenient.

The first curvature adjustment knob 12 and/or the second curvature adjustment knob 13 will not directly resist against the housing 11. A ring 111 may be arranged between the first curvature adjustment knob 12 and/or the second curvature adjustment knob 13 and the housing 11. The ring 111 is fixedly connected to the housing 11, and the first curvature adjustment knob 12 or the second curvature adjustment knob 13 resists against the ring 111. Relative rotation between the first curvature adjustment knob 12 or the second curvature adjustment knob 13 and the ring 111 can be achieved. The fixed connection may be fastened connection or glued fixing. Adding the ring 111 may increase the size of the handle 1 and also plays a role of decoration.

In other embodiments, the first curvature adjustment knob 12 and/or the second curvature adjustment knob 13 are located in the middle part of the housing 11. That is, the middle part of the housing 11 is cut off to form a plurality of housing portions. The first curvature adjustment knob 12 and the second curvature adjustment knob 13 respectively resist against the adjacent housing parts and may relatively rotate.

The housing 11 is approximately of a columnar structure. The middle part of an outer wall of the housing 11 is inwards sunken, and an outer diameter of the middle part of the outer wall of the housing 11 is less than that of two ends of the outer wall of the housing 11, which is convenient for the operator to hold. Optionally, the outer wall of the housing 11 may be provided with an antiskid line 110 which is convenient for operation.

Figure 2:
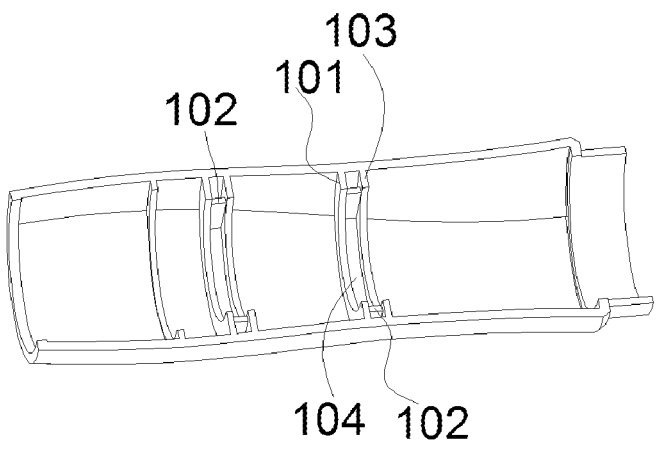
FIG. 2 is a partially schematic diagram of a housing of a bendable sheath provided by one embodiment.

In FIG. 2, a plurality of groups of arc-shaped protrusions are arranged inside the housing 11, each group of which includes two adjacent arc-shaped protrusions 101, 103. An arc-shaped groove 104 is formed between the two adjacent arc-shaped protrusions 101, 103. Two ends of the arc-shaped groove 104 are provided with two groove stop pieces 102. In this embodiment, for facilitating machining and assembling, the housing 11 may be halved from the middle. That is, the housing includes a first housing and a second housing. A plurality of fastener structures are arranged at a junction between the first housing and the second housing. The first housing and the second housing are fastened with each other to form a columnar housing. The first housing and the second housing may also be integrated.

Figure 3:
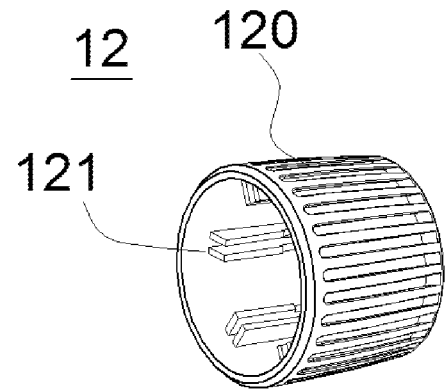
FIG. 3 is a schematic diagram of a first curvature adjustment knob of a bendable sheath provided by one embodiment.

Referring to FIG. 3, the first curvature adjustment knob 12 is of a ring structure, and a diameter of an opening in the distal end of each ring structure and a diameter of an opening in the distal end of the ring structure may be the same or different, which can be designed according to the appearance of the handle. An outer wall of the first curvature adjustment knob is provided with an antiskid member 120, such as a stripe structure, a thread structure, and a convex block structure. An inner wall of the first curvature adjustment knob 12 is provided with a clamping slot structure 121. The second curvature adjustment knob 13 has the same structure as that of the first curvature adjustment knob 12. The sizes of the second curvature adjustment knob 13 and the first curvature adjustment knob 12 may be the same or different.

Figure 4:
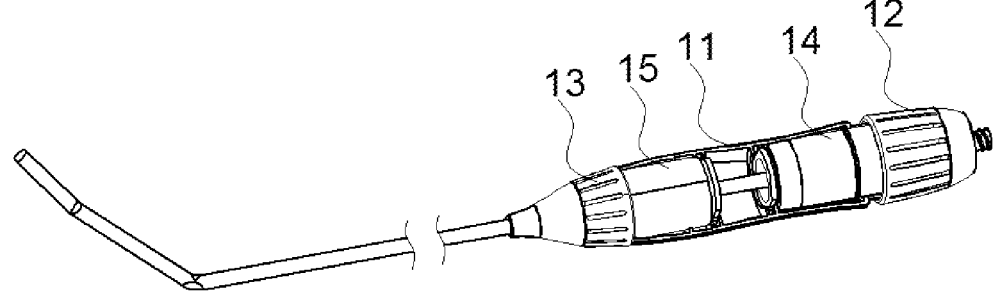
FIG. 4 is a partially schematic diagram of a bendable sheath provided by one embodiment.

Referring to FIG. 4, the handle 1 further includes a first bend adjustment module 14 and a second bend adjustment module 15. A distal end of the first bend adjustment module 14 is opposite to a proximal end of the second bend adjustment module 15. The first bend adjustment module 14 is arranged in the housing 11 and the first curvature adjustment knob 12, and the second bend adjustment module 15 is arranged in the housing 11 and the second curvature adjustment knob 13.

Figure 5:
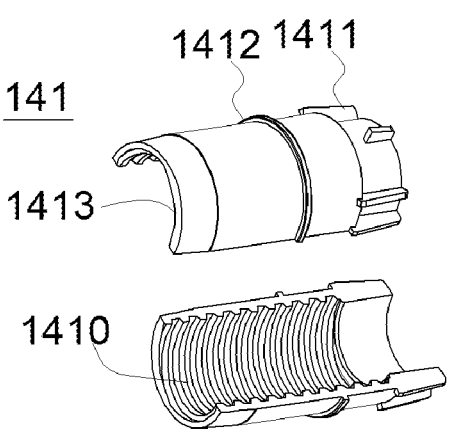
FIG. 5 is a schematic diagram of a first transmission thread bushing of a bendable sheath provided by one embodiment.
Figure 6:
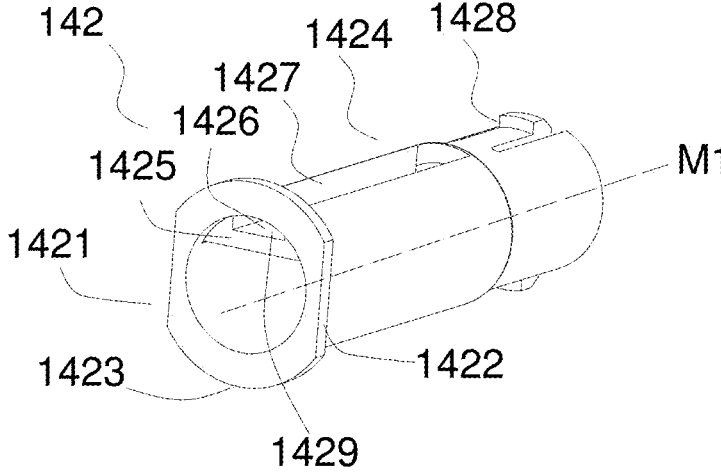
FIG. 6 is a schematic diagram of a first guide rail member of a bendable sheath provided by one embodiment.
Figure 7:
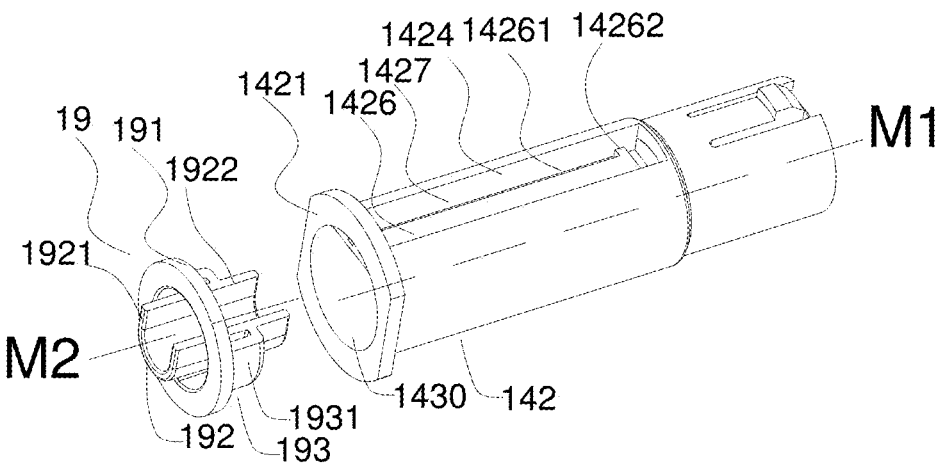
FIG. 7 is a schematic diagram of a first guide rail member and a support member of a bendable sheath provided by one embodiment.

Referring to FIG. 5, FIG. 6, and FIG. 7, the first bend adjustment module 14 includes a first transmission thread bushing 141, a first guide rail member 142, and a first slider 143. The first slider 143 is slidably arranged on the first guide rail member 142, and the first transmission thread bushing 141 is sleeved on the first guide rail member 142 and the first slider 143.

Referring to FIG. 5, the first transmission thread bushing 141 is cylindrical. In order to facilitate machining and assembling, like the housing 11, the first transmission thread bushing 141 may be halved from the middle or may be integrated. An inner wall of the first transmission thread bushing 141 is provided with a thread structure 1410, and an outer wall of the first transmission thread bushing 141 is provided with a convex block structure 1411. With reference to FIG. 3 and FIG. 5, the convex block structure 1411 is matched with the clamping slot structure 121 on the inner wall of the first curvature adjustment knob 12 to fixedly connect the first transmission thread bushing 141 with the first curvature adjustment knob 12. It can be understood that in one embodiment, the outer wall of the proximal end of the first transmission thread bushing 141 may be provided with the clamping slot structure, and the inner wall of the first curvature adjustment knob 12 may be provided with the convex block structure. The clamping slot structure is matched with the convex block structure. In one embodiment, the first curvature adjustment knob 12 and the first transmission thread bushing 141 are directly fixedly connected with each other by glue. In this embodiment, the convex block structure 1411 on the outer wall of the first transmission thread bushing 141 is located at the proximal end of the first transmission thread bushing 141. In other embodiments, the convex block structure 1411 may be also located at the middle part or distal end of the first transmission thread bushing 141. The position of the convex block structure 1411 is set according to the position of the first curvature adjustment knob 12. In this embodiment, the outer wall of the first transmission thread bushing 141 is further provided with a ring convex block 1412. It can be understood that the inner wall of the housing 11 is provided with a groove structure matched with the ring convex block 1412, thus avoiding an axial movement of the first transmission thread bushing 141 in the housing 11. However, the first transmission thread bushing 141 can be allowed to rotate with respect to the housing.

In this embodiment, the first curvature adjustment knob 12 and the first transmission thread bushing 141 form a first gyration subassembly. It can be understood that in other embodiments, the handle 1 may not include the first curvature adjustment knob 12, and the first gyration subassembly may not include the first curvature adjustment knob 12, and only includes the first transmission thread bushing 141. The first slider does a reciprocating movement on the first guide rail member by means of directly gyrating the first transmission thread bushing 141.

A distal end or proximal end of the first guide rail member is provided with a catch structure that is abutted with the housing to avoid axial and radial movements of the first guide rail member. For example, referring to FIG. 6, the first guide rail member 142 has a tube cavity structure. The catch structure is arranged at an opening of a distal end of the first guide rail member 142. The catch structure is a "track-type" ring protrusion portion 1421. A periphery of the "track-type" ring protrusion portion 1421 includes two sections of arc-shaped portion 1423 and two sections of straight-line portions 1422. The arc-shaped portion 1423 and the straight-line portions 1422 are alternately connected to form an appearance similar to a "track". With reference to FIG. 2 and FIG. 6, the "track-type" ring protrusion portion 1421 is matched with the plurality of arc-shaped grooves 104 arranged inside the housing 11. For example, the arc-shaped portion 1423 of the "track-type" ring protrusion portion 1421 are clamped in the arc-shaped grooves 104 arranged inside the housing 11, and the straight-line portions 1422 of the "track-type" ring protrusion portion 1421 resist against the groove stop pieces 102 at the two ends of the arc-shaped grooves 104 to fix the first guide rail member 142 and the housing 11 and avoid the axial and radial movements of the first guide rail member 142. In other embodiments, the "track-type" ring protrusion portion may be replaced with a round ring protrusion portion. The two ends of the arc-shaped grooves 104 arranged inside the housing 11 may not be provided with the stop pieces, and the round ring protrusion portion is directly clamped in the arc-shaped grooves 104.

The first guide rail member 142 is arranged in the first transmission thread bushing 141. The first transmission thread bushing 141 is arranged in the housing 11. With reference to FIG. 2 and FIG. 5, a distal end 1413 of the first transmission thread bushing 141 resists against a side wall of the arc-shaped protrusion 103, close to the proximal end, of the two arc-shaped protrusions arranged inside the housing 11 to play a limiting role.

Referring to FIG. 6 again, a first groove 1424 is axially arranged on an outer wall of the first guide rail member 142; at least part of the outer wall of the first guide rail member 142 is radially sunken towards a center axis M1 of the first guide rail member 142 to form the first groove 1424. The first groove 1424 includes a first bottom 1426 and two first side walls 1427. The first groove 1424 forms a track, a length of which determines a range of a bending angle of a bent position on the sheath body. In this embodiment, the first groove 1424 is linear. In another embodiment, the first groove 1424 may also be an arc shape extending from the proximal end to the distal end. In other embodiments, the first groove 1424 may also be arranged on an outer surface of the first guide rail member 142. The first side walls 1427 are located on the outer surface of the first guide rail member 142. The first bottom 1426 is at least part of the outer surface of the first guide rail member 142.

In this embodiment, a distal end 1425 of the first groove is located at the distal end of the first guide rail member 142. The first ring protrusion portion 1421 and the distal end 1425 of the first groove 1424 are encircled into a first opening 1429 that is used for allowing a first traction wire to pass through. A position of the distal end 1425 of the first groove that is in contact with the first traction wire may be set to be a circular-arc-shaped structure, thereby avoiding an edge of the distal end 1425 of the first groove from abrading the first traction wire, so that the service life of the first traction wire is prolonged.

In one embodiment, the distal end 1425 of the first groove may be located in the middle of the first guide rail member 142. In one embodiment, the first opening 1429 may be formed in any position on the first guide rail member 142. For example, the position of the first groove 1424 close to the distal end, the distal end of the first groove 1424, the position of the first groove 1424 close to the proximal end, the proximal end of the first groove 1424, or the first guide rail member 142 may not be provided with the first opening 1429, and the proximal end of the first traction wire passes through a wall of the sheath body, directly enters the first groove, and is connected to the first slider.

The proximal end of the first guide rail member 142 is provided with a first connection member 1428. With reference to FIG. 1 and FIG. 6, the first connection member 1428 and the first guide rail member 142 are of an integrated structure or are fixedly connected. The first connection member 1428 is screwed or fastened to the rear end cover 16.

Optionally, the first groove is provided with a slideway; the first slider slides on the slideway. In this embodiment, referring to FIG. 7, the slideway is a groove slideway 14261. The first bottom 1426 of the first groove 1424 is provided with two groove slideways 14261 which are parallel to the two first side walls 1427 and have a length approximately the same as a length of the first side walls 1427. In other embodiments, the groove slideway 14261 may be a curve shape or a broken line shape. The groove slideways 14261 do not need to be parallel to the two first side walls 1427. The lengths of the groove slideways 14261 and the lengths of the first side walls 1427 may also be different.

Two ends of the groove slideways 14261 are respectively provided with slideway stop pieces 14262. A surface (1436 in FIG. 10) of the first slider opposite to the first bottom 1426 of the first groove 1424 is provided with a protrusion sliding member (specifically referring to the structure of the first slider below). The first slider slides between the slideway stop pieces 14262 of the groove slideways 14261, so as to control a sliding range of the first slider and avoid the first slider from being separated from the first groove 1424. In this embodiment, the two groove slideways 14261 are respectively close to the two first side walls 1427. In other embodiments, at least any one of the two groove slideways 14261 may be arranged at a position of the first bottom 1426 close to the middle, or the number of the groove slideways 14261 may be one or more.

In another embodiment, the first side wall 1427 of the first groove 1424 is provided with a groove slideway, and a surface (referring to 1437 in FIG. 9 or FIG. 10) of the first slider opposite to the first side wall 1427 of the first groove 1424 is provided with a protrusion sliding member. The protrusion sliding member slides in the groove slideway. Two ends of the groove slideway may be respectively provided with slideway stop pieces.

In other embodiments, the slideway may also be a protrusion slideway, and the first slider is provided with a sliding groove cooperatively connected with the protrusion slideway. The first slider slides on the slideway. In other embodiments, any position on the slideway is provided with at least two slideway stop pieces. The first slider slides between any two slideway stop pieces.

Figure 9:
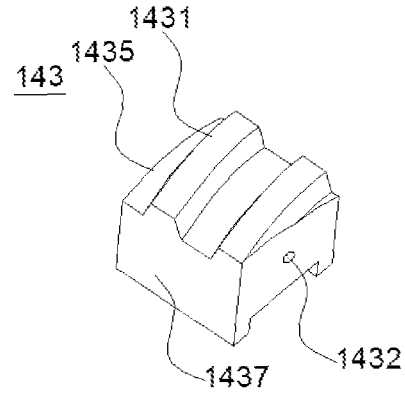
FIG. 9 is a schematic diagram of a first slider of a bendable sheath provided by one embodiment.

Referring to FIG. 9, the first slider 143 is approximately cubic. A first surface 1435 of the first slider 143 is provided with a first thread structure 1431. With reference to FIG. 5 and FIG. 9, the first surface 1435 is opposite to the inner wall of the first transmission thread bushing 141. The first thread structure 1431 of the first surface 1435 of the first slider 143 is matched with the thread structure 1410 arranged inside the first transmission thread bushing 141.

Figure 10:
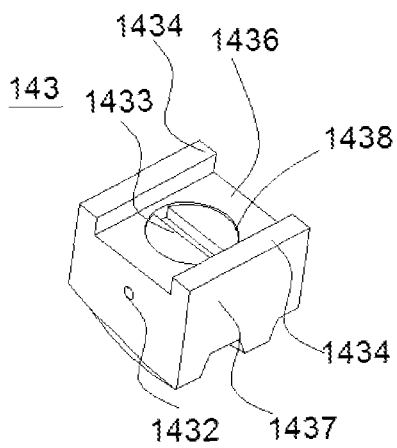
FIG. 10 is a schematic diagram of another view of a first slider of a bendable sheath provided by one embodiment.

The first slider 143 is provided with a sliding member. With reference to FIG. 7 and FIG. 10, in this embodiment, the sliding member is a protrusion sliding member 1434. A second surface (the surface 1436 opposite to the first bottom 1426 of the first groove 1424) of the first slider 143 is provided with two protrusion sliding members 1434. The two protrusion sliding members 1434 are matched with the two groove slideways 14261 arranged in the first groove 1424 so that the first slider 143 can axially slide in the first groove 1424. By the arrangement of the sliding members 1434 and the groove slideways 14261, a contact area of the bottom of the first slider 143 and the first groove 1424 can be reduced, thereby reducing friction and facilitating operations.

Referring to the description of the first groove 1424 of the first guide rail member 142, in one embodiment, the sliding member includes a sliding groove. In another embodiment, the second surface of the first slider 143 provided with the sliding member may also be the surface 1437 opposite to the first side wall 1427 of the first groove 1424.

In FIG. 10, the first slider 143 is further provided with an accommodating slot 1438 and a through hole 1432. The accommodating slot 1438 is communicated with the through hole 1432. A fixing member is arranged in the accommodating slot 1438. The fixing member may be a screw or a fixing member made of other materials, as long as it can be fixed in the accommodating slot 1438. In this embodiment, the fixing member is a screw 1433. One end of the first traction wire is connected with the screw 1433 after being threaded in from the through hole 1432, thereby fixing one end of the first traction wire. In one embodiment, an opening of the accommodating slot 1438 may be formed in any surface of the first slider 143 except for the first surface 1435, as long as the first traction wire can be fixed. One end of the first traction wire is connected with the screw 1433 by glue. Or, one end of the first traction wire is wound on the screw 1433.

Figure 11:
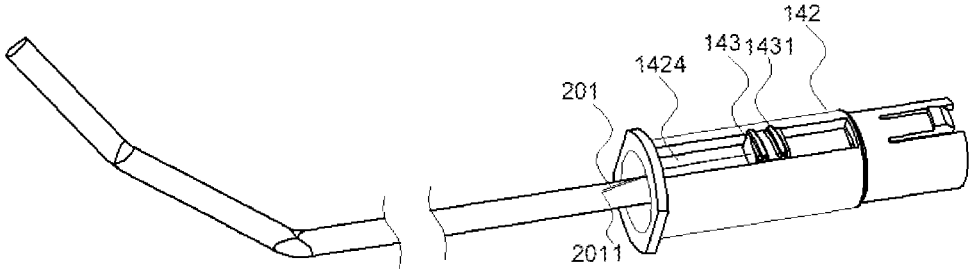
FIG. 11 is a schematic diagram of mutual cooperation of a first guide rail member, a first slider, and a sheath body of a bendable sheath provided by one embodiment.

Referring to FIG. 11, the first slider 143 is arranged in the first groove 1424 of the first guide rail member 142. When the first curvature adjustment knob 12 is rotated, the first transmission thread bushing 141 is driven to rotate, thus driving the first slider 143 to rotate. Since the first slider 143 is arranged in the first groove 1424 of the first guide rail member 142, the rotation of the first slider 143 is restrained. Therefore, the first slider 143 slides in a direction of the first groove 1424 of the first guide rail member 142 and will not rotate together with the first transmission thread bushing 141.

It can be understood that in one embodiment, the handle may not include the first curvature adjustment knob 12 and the first transmission thread bushing 141. In other ways, for example, the first slider 143 is directly manually operated to slide in the first groove 1424 of the first guide rail member 142, thus driving the first traction wire to move.

One end of the first traction wire 201 is fixedly connected with the first slider 143, and the other end of the first traction wire 201 extends towards the distal end along the first groove 1424, then passes through the distal end of the first groove 1424, and enters the sheath body from an open pore 2011 in the wall of the sheath body 2. The open pore 2011 is close to the distal end of the first groove 1424. As the first slider 143 slides, the first traction wire 201 is driven to move.

Referring to FIG. 7 again, a support member 19 matched with the first guide rail member 142 includes a first catch part 191, a first collecting part 192, and a second collecting part 193. The first catch part 191 and the second catch part 193 are axially connected, and the first collecting part 192 axially penetrates through the first catch part 191 and the second catch part 193.

The first catch part 191 is of a ring structure. When the support member 19 is inserted into the first guide rail member 142, since an outer diameter of the first catch part 191 is greater than an inner diameter of the tube cavity structure of the first guide rail member 142, a proximal end face of the first catch part 191 resists against a distal end face of the "track-type" ring protrusion portion 1421 at the opening in the distal end of the first guide rail member 142. In other embodiments, the support member 19 may be arranged at a proximal portion of the first guide rail member 142, and the first catch part 191 resists against a proximal end face of the first guide rail member.

A radial section of the first collecting part 192 is approximately of a U-shaped structure. The first collecting part 192 is at least partially arranged in the tube cavity structure of the first guide rail member 142. In this embodiment, the first collecting part 192 includes a first portion 1921 and a second portion 1922. The first portion 1921 and the second portion 1922 are axially connected. When the support member 19 is inserted into the first guide rail member 142, due to the restriction of the first catch part 191, the first portion 1921 is arranged outside the tube cavity of the first guide rail member 142, and the second portion 1922 is arranged inside the tube cavity of the first guide rail member 142. The second portion 1922 and at least part of the first bottom 1426 of the first groove 1424 form a channel space. An axial center axis M2 of the channel space is parallel to or coaxial with an axial center axis M1 of the tube cavity of the first guide rail member 142. After the proximal end of the sheath body passes through the channel space, the channel space can collect and support the sheath body to further fix the proximal end of the sheath body. In other embodiments, the first catch part 191 and the first collecting part 192 are axially connected, and the first collecting part 192 can also be entirely located in the tube cavity of the first guide rail member 142. In other embodiments, the first collecting part 192 may be a hollow tubular structure. An outer diameter of the tubular structure of the first collecting part 192 is the same as the inner diameter of the sheath body.

Optionally, the support member 19 further includes the second catch part 193. The second catch part 193 wraps the portion (the second portion 1922) of the first collecting part 192 arranged in the tube cavity of the first guide rail member 142. The second catch part 193 has an arc-shaped outer surface 1931. When the support member 19 is inserted into the first guide rail member 142, the second catch part 193 enters the tube cavity of the first guide rail member 142. The arc-shaped outer surface 1931 is fitted to at least part of the region of an inner surface 1430 of the tube cavity of the first guide rail member 142.

Figure 8:
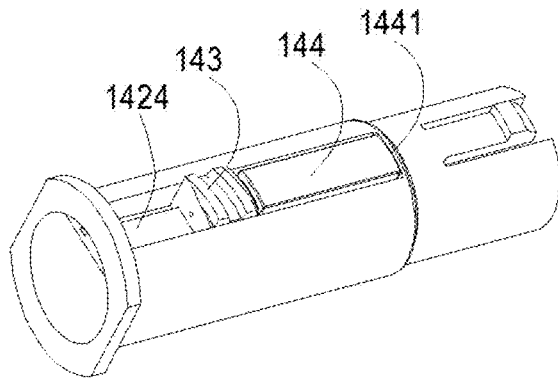
FIG. 8 is a schematic diagram of a first guide rail member, a first slider, and a stopper of a bendable sheath provided by one embodiment.

When the inner diameter of the tube cavity of the first guide rail member 142 is relatively large, the diameter of the sheath body is relatively small, and the outer diameter of the first collecting part 192 is relatively small, the second catch part 193 has an effect of supporting the first collecting part 192 in the tube cavity of the first guide rail member 142. In one embodiment, the first collecting part 192 and the second catch part 193 may be combined into a whole serving as the first collecting part. When the inner diameter of the tube cavity of the first guide rail member 142, the diameter of the sheath body is relatively large, and the outer diameter of the first collecting part 192 is also relatively large, the second catch part 193 may also not be provided, and an outer wall of the first collecting part 192 is directly fitted to at least part of the region of the inner surface 1430 of the tube cavity of the first guide rail member 142. Optionally, the first guide rail member further includes a stopper that is arranged in the first groove to cut off the first groove, so as to restrain a sliding distance of the first slider, thus controlling a range of a bending angle of the sheath body. For example, referring to FIG. 8, the stopper is a stop block 144. A proximal end 1441 of the stop block 144 resists against the proximal end of the first groove 1424 to adjust the length of the first groove 1424, thus controlling the sliding distance of the first slider 143. The number of the stop block 144 is 1. The length of the stop block 144 is adjustable. For example, the stop block may be shortened or extended. The length of the stop block 144 is adjusted to match a desired length of the first groove 1424. The number of the stop block 144 is plural. The length of each stop block 144 is different. The stop blocks 144 with different lengths are selected to match different lengths of the first groove 1424. The stopper may be a baffle plate. Two ends of the baffle plate may be clamped between the two first side walls of the first groove 1424. The sliding distance of the first slider is adjusted by adjusting the position of the baffle plate.

Similarly, the second bend adjustment module 15 includes a second transmission thread bushing (not shown), a second guide rail member 152, and a second slider 153.

Figure 12:
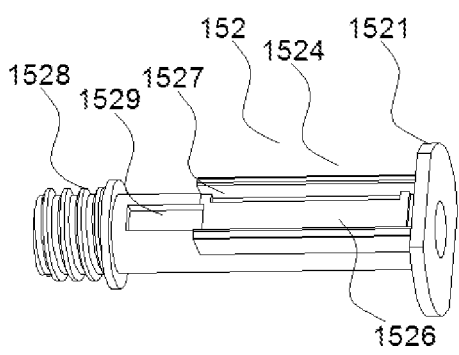
FIG. 12 is a schematic diagram of a second guide rail member of a bendable sheath provided by one embodiment.

Referring to FIG. 12, a "track-type" ring protrusion portion 1521 is arranged at an opening of a proximal end of the second guide rail member 152. A distal end of the second guide rail member 152 is provided with a second connection member 1528. The second connection member 1528 and the second guide rail member 152 are of an integrated structure or are fixedly connected.

A second groove 1524 is axially formed in an outer wall of the second guide rail member 152. The second groove 1524 is provided on an outer surface of the second guide rail member 152. The second groove 1524 includes a second bottom 1526 and two second side walls 1527. The second side walls 1527 are located on the outer surface of the second guide rail member 152. The second bottom 1526 is at least part of the outer surface of the second guide rail member 152. In another embodiment, similar to the structure of the first groove 1424 on the first guide rail member 142, at least part of the outer wall of the second guide rail member 152 may be radially sunken towards a center axis of the second guide rail member 152.

In this embodiment, a position of the second guide rail member 152 close to the distal end of the second groove 1524 or the distal end of the second groove 1524 is provided with a second opening 1529. The second opening 1529 is communicated with a tube cavity structure of the second guide rail member 152. In other embodiments, the second opening may be provided at any position on the second guide rail member 152 or no second opening is provided. The specific content refers to the first guide rail member.

Figure 13:
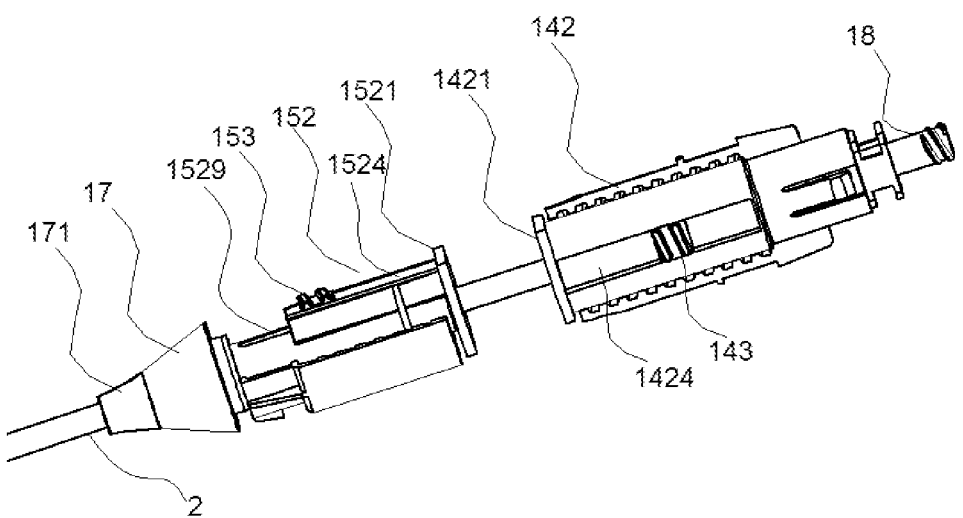
FIG. 13 is another partially schematic diagram of a bendable sheath provided by one embodiment.

In FIG. 13, one end of the second traction wire is fixedly connected with the second slider 153, and the other end of the second traction wire extends towards the distal end along the second groove 1524, passes through the distal end of the second groove 1524, enters the second opening 1529, is threaded into the outer wall of the sheath body 2, and enters the sheath body. As the second slider 153 slides, the distal end of the second traction wire is driven to move.

In this embodiment, the "track-type" ring protrusion portion 1521 arranged at the opening in the proximal end of the second guide rail member 152 is opposite to the "track-type" ring protrusion portion 1421 of the first guide rail member 142. The second connection member 1528 arranged at the distal end of the second guide rail member 152 is screwed or fastened to the front end cover 17. The proximal end of the sheath body 2 is threaded in from the protective sleeve 171 at the distal end of the front end cover 17 and then passes through the second guide rail member 152 and the first guide rail member 142 in sequence till it is connected to a threaded connection head 18 at the proximal end. The threaded connection head 18 is used for being connected to an exhaust device.

Figure 14:
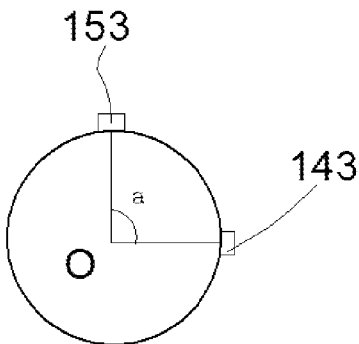
FIG. 14 is a schematic diagram of observation of FIG. 13 in a direction from a distal end to a proximal end.

A lengthwise direction of the second groove 1524 and a lengthwise direction of the first groove 1424 arranged on the outer wall of the first guide rail member 142 are not on the same straight line. That is, a movement trajectory of the first slider 143 and a movement trajectory of the second slider 153 are not on the same straight line. Referring to FIG. 14, in a direction from the distal end to the proximal end, in this embodiment, an included angle a between a perpendicular distance from the first slider 143 and an axis O of the handle and a perpendicular distance from the second slider 153 and the axis O of the handle is 90 degrees. In other embodiments, the included angle a is not equal to 0 degree. This arrangement aims to avoid mutual interference between the first traction wire 201 and the second traction wire (connected with the second slider 153).

In this embodiment, the second curvature adjustment knob 13 and the second transmission thread bushing form a second gyration subassembly. It can be understood that in other embodiments, the handle 1 may not include the second curvature adjustment knob 13, that is, the second gyration subassembly may not include the second curvature adjustment knob 13, and only includes the second transmission thread bushing. The second slider does a reciprocating movement on the second guide rail member by means of directly gyrating the second transmission thread bushing.

In this embodiment, for other structures, the second bend adjustment module 15 is the same as the first bend adjustment module 14. It can be understood that the structure in the housing 11 having a cooperation relation with the first bend adjustment module 14 or the structure on the first curvature adjustment knob 12 is correspondingly the same structure as the structure in the housing 11 having a cooperation relation with the second bend adjustment module 15 or the structure on the second curvature adjustment knob 13. In other embodiments, the second bend adjustment module 15 may be completely the same as the first bend adjustment module 14.

In one embodiment, the sheath body of the bendable sheath 100 may have a plurality of bendable positions, such as three or more bendable positions. The handle correspondingly includes three or more bend adjustment modules. The three or more bend adjustment modules are axially placed on the same straight line, and the proximal end of the sheath body sequentially passes through the three or more bend adjustment modules.

In one embodiment, the sheath body of the bendable sheath 100 may also have only one bendable position, and the handle correspondingly only includes one bend adjustment module. The proximal end of the sheath body passes through the bend adjustment module.

Referring to FIG. 1 again, in this embodiment, the bendable sheath 100 is a dual-bendable sheath, a distal end portion of the sheath body of which includes two bendable sections, i.e., a first section 21 and a second section 22. The first traction wire is connected to the first section 21, and the second traction wire is connected to the second section 22. The sheath body 2 further includes a third section 23, a fourth section 24, and a fifth section 25. In FIG. 1, a connection order from the distal end to the proximal end is the four section 24, the second section 22, the third section 23, the first section 21, and the fifth section 25.

The hardness of the third section 23 is greater than that of the first section 21 and that of the second section 22. The harder third section 23 is arranged between the two bendable sections (the first section 21 and the second section 22), so that when the second traction wire drives the second section 22 to bend, the first section 21 is avoided from being driven to bend, thereby avoiding the second section 22 from affecting the bending of the first section 21, resulting in inaccurate bending.

The hardness of the fourth section 24 located at the distal end of the sheath body 2 is greater than that of the second section 22. When the distal end of the sheath body 2 is conveyed to a target position (such as the left atrial appendage) by means of curvature adjustment, and the fourth section 24 located at the distal end of the sheath body 2 will not bend under the influence of the bending of the second section 22, so that it is easier to keep the distal end of the sheath body 2 being coaxial with the target position, thus achieving more accurate release.

It can be understood that when the sheath body of the bendable sheath 100 is provided with only one bendable position, the sheath body includes a distal section, a bendable section, and a proximal section connected in sequence from the distal end to the proximal end. The traction wire is connected with the bendable section, and the hardness of the distal section is greater than that of the bendable section. When the bendable section bends, the distal section will not be driven to bend, so that it is easier to keep the distal end of the sheath body being coaxial with the target position, thus achieving more accurate release.

Figure 15:
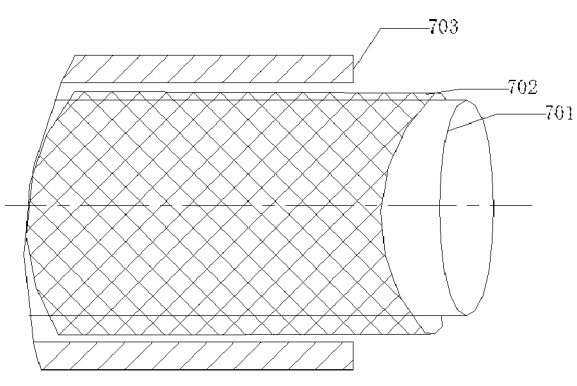
FIG. 15 is a structural enlarged diagram of part of a sheath body of a bendable sheath provided by one embodiment.
Figure 16:
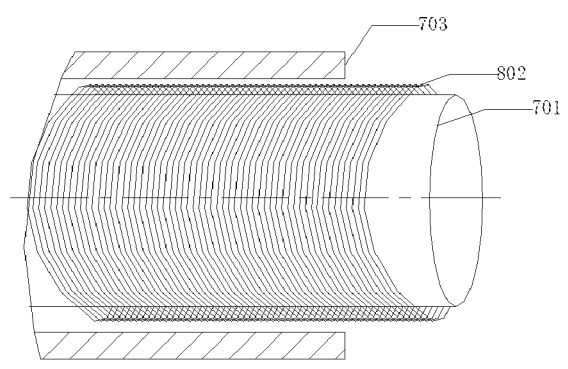
FIG. 16 is a structural enlarged diagram of part of a sheath body of a bendable sheath provided by another embodiment.

Referring to FIG. 15 and FIG. 16, in this embodiment, the sheath body 2 is made of a composite material. The sheath body 2 includes an inner-layer tube 701, an intermediate layer, and an outer-layer tube 703. The inner-layer tube 701 and the outer-layer tube 703 are tube bodies made of high-molecular materials, and the intermediate layer is a woven net tube 702 or a bourdon tube 802. The sheath body 2 is of an integrated tubular structure formed by thermally melting the three layers of structures.

The inner-layer tube 701 adopts a high-molecular material with high lubricity and low friction, such as polytetrafluoroethylene (PTFE) and high density polyethylene (HDPE), an inner surface of which is smooth, which can ensure that other apparatuses smoothly pass through the inner surface. The outer-layer tube 703 is formed by splicing high-molecular materials with different hardnesses, such as PABAX with different hardnesses and polyamide (PA) tubes with different hardnesses.

The woven net tube 702 of the intermediate layer is formed by weaving a metal wire by using a knitting machine. In the process of manufacturing the sheath body 2, one section of woven net tube is cut down and is laced and pasted on an outer surface of the inner-layer tube 701, and the outer-layer tube 703 is sleeved on it for thermal melting into the integrated tube cavity structure. Similarly, the bourdon tube 802 of the intermediate layer is wound by a spring machine for winding a spring, but the process of manufacturing the sheath body 2 is the same as that of the woven net tube.

In this embodiment, referring to FIG. 1 again, the sheath body 2 may be pre-molded. The thermally molten sheath body is placed in a plastic mold to mold a desired molding angle state. For example, the first section 21 and/or the second section 22 are pre-molded into curved states. Under the control of the handle 1, the first section 21 and/or the second section 22 is further curved within a certain radian range. In one embodiment, the sheath body 2 may also be a straight tube.

A first fixing ring and a second fixing ring are arranged in the sheath body 2. The first traction wire is connected to the first fixing ring; the first fixing ring is arranged at the first section 21; the second traction wire is connected to the second fixing ring; and the second fixing ring is arranged at the second section 22. The first fixing ring is sleeved on an outer surface of the intermediate layer of the sheath body 2 and is embedded into the outer-layer tube 703 of the sheath body 2.

Figure 17:
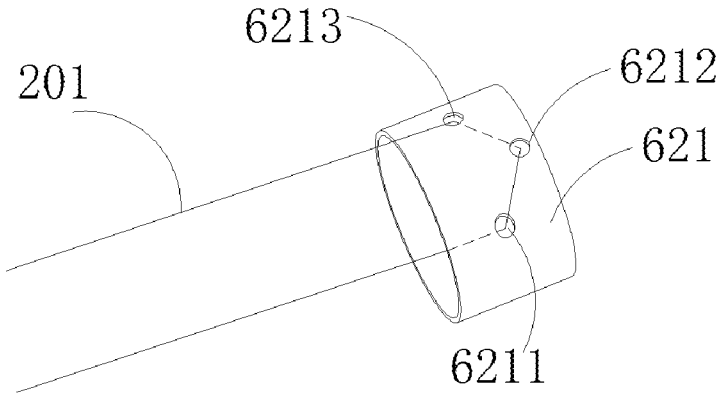
FIG. 17 is a schematic diagram of connection between a first pull guide wire and a first fixing ring provided by one embodiment.

Referring to FIG. 17, a side wall of the first fixing ring 621 is provided with a first hole 6211, a second hole 6212, and a third hole 6213. The second hole 6212 is closer to the distal end of the first fixing ring 621 than the first hole 6211 and the third hole 6213. The proximal end of the first traction wire 201 is connected to the first slider, and the distal end of the first traction wire 201 passes through the first hole 6211, the second hole 6212, and the third hole 6213 in sequence or passes through the third hole 6213, the second hole 6212, and the first hole 6211 in sequence, extends towards the proximal end along the sheath body 2, and is connected to the first slider again.

Figure 18:
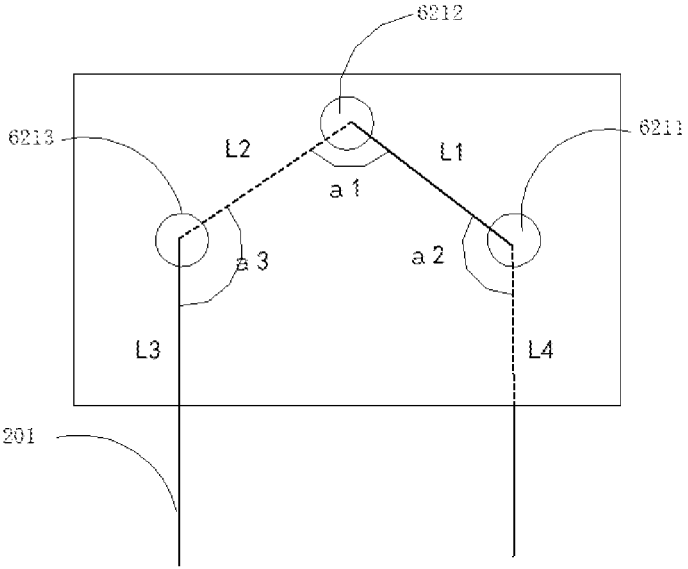
FIG. 18 is a schematic diagram of another view of FIG. 17.

Referring to FIG. 18, a first connecting line L1 is reserved between a center of the first hole 6211 and a center of the second hole 6212, and a second connecting line L2 is reserved between a center of the third hole 6213 and the center of the second hole 6212. An included angle a1 between the first connecting line L1 and the second connecting line L2 is an obtuse angle. An included angle a2 is formed between the first connecting line L1 and Section L4 of the first traction wire 201, and an included angle a3 is formed between the second connecting line L2 and Section L3 of the first traction wire 201, where a2 and a3 are both obtuse angles. In this way, stress concentration of the first traction wire can be avoided, thereby prolonging the service life.

Similarly, a side wall of the second fixing hole is provided with a fourth hole, a fifth hole, and a sixth hole. The fifth hole from among the fourth hole, the fifth hole, and the sixth hole is closer to the distal end. The structure is the same as that of the first fixing ring 621. Descriptions thereof are omitted here.

In this embodiment, a direction to which the side wall of the first fixing ring 621 provided with the first hole 6211, the second hole 6212, and the third hole 6213 faces and a direction to which the side wall of the second fixing ring provided with the fourth hole, the fifth hole, and the sixth hole faces are not the same direction. With reference to what is mentioned in the handle, the lengthwise direction of the second groove 1524 and the lengthwise direction of the first groove 1424 arranged on the outer wall of the first guide rail member 142 are not on the same straight line. That is, the movement trajectory of the first slider 143 and the movement trajectory of the second slider 153 are not on the same straight line. Meanwhile, the first traction wire and the second traction wire are parallel to each other in the sheath body. As a whole, in addition to the above-mentioned description that the mutual interference between the first traction wire and the second traction wire can be avoided, it can be implemented that the bending directions of the first section 21 connected to the first traction wire and the second section 22 connected to the second traction wire are different, so that the sheath body of the bendable sheath 100 can bend in multiple directions and can be accurately released in a complex situation, which is convenient for operation.

It can be understood that the first fixing ring may not be provided with a hole structure. One end of the first traction wire is connected to the first slider, and the other end of the first traction wire passes through the first fixing ring along the inner wall of the first fixing ring, reaches the distal end of the first fixing ring, and then extends along the outer wall of the first fixing ring till it is connected to the first slider again. The second fixing ring may also be disposed in this way, and descriptions thereof are omitted here.

In order to further prolong the fatigue life cycle of connection between the traction wire and the fixing ring, a high-strength traction wire material may be adopted, such as a carbon fiber wire, or a high-strength NiTi multi-strand wire. Compared to a NiTi single wire with an equal outer diameter, the NiTi multi-strand wire has lower fatigue stress, so that when it is connected to the fixing ring, breakage caused by a concentrated fatigue stress is unlikely to occur. Even if one wire is broken, other wires may also adjust the angle of the sheath body, and the service life of the traction wire can be prolonged. Meanwhile, if one wire is broken, a pre-warning sound "bang" will be made to remind an operator that "the traction wire of the bendable conveying sheath has been broken. Be careful. End this operation process as soon as possible".

Figure 19:
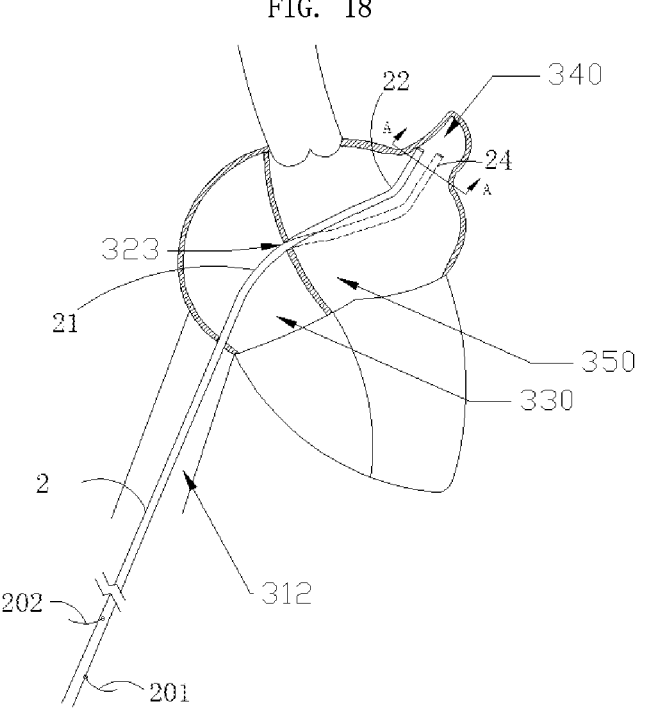
FIG. 19 is a schematic diagram of operation that a bendable sheath provided by one embodiment is put into the heart.
Figure 20:
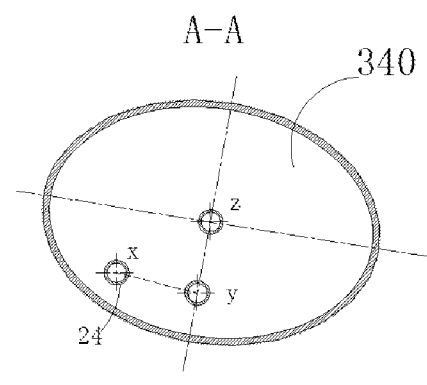
FIG. 20 is a cutaway view of A-A in FIG. 19.

In this embodiment, a left atrial appendage occluder being released in the left atrial appendage is taken as an example. An operation process of the bendable sheath 100 is as follows:

Referring to FIG. 19, the dual-bendable sheath 100 reaches the right atrium 330 via the inferior vena cava 312, passes through an atrial septum puncture point 323, and reaches the left atrium 350. At this time, the fourth section 24 located at the distal end of the sheath body 2 is fitted to the inner wall of the left atrial appendage 340. The fourth section 24 and the left atrial appendage 340 are not coaxial. It can be seen from FIG. 20 that the position of the fourth section 24 after it passes through the atrial septum 323 is x.

In order to adjust the fourth section 24 at the distal end of the sheath body 2 to be coaxial with the left atrial appendage 340. The first curvature adjustment knob 12 on the handle is gyrated to apply a force to the first traction wire 201; and the first traction wire 201 adjusts the angle of the first section 21 so that the fourth section 24 moves from position x to position y to reach a lateral mid-point of the left atrial appendage 340.

The second curvature adjustment knob 13 on the handle is gyrated to apply a force to the second traction wire 202. The second traction wire 202 adjusts the angle of the second section 22 so that the fourth section 24 moves from position y to position z to reach the left atrial appendage 340. At this point, the fourth section 24 at the distal end of the sheath body 2 is completely coaxial with the left atrial appendage 340, and the fourth section 24 at the distal end of the sheath body 2 is located at position z.

When the angle and position of the sheath body 2 are fixed, the operator can quickly convey, release, and withdraw the left atrial appendage occluder. In the whole process, the operative time is short, and the safety is high.

According to the bendable sheath provided by this embodiment, the coaxiality of the sheath body and a target lesion position is good, and the medical apparatus can smoothly reach the target lesion position. After being released, the medical apparatus can be firmly fixed in a target lesion region. Meanwhile, the dependence on the experience of the operator who delivers the medical apparatus is effectively reduced, s that the operator can use the bendable sheath to deliver and release the medical apparatus at will after simple training.

Figure 21:
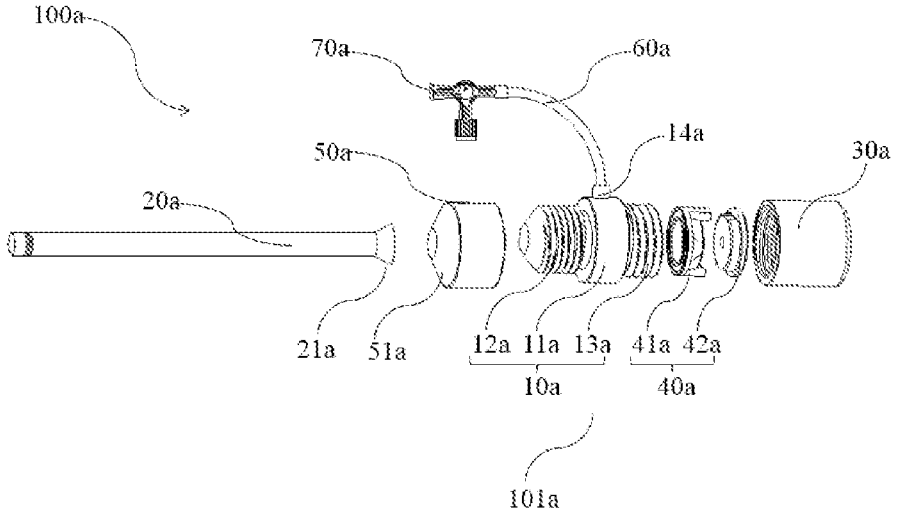
FIG. 21 is a schematic diagram of an exploded structure of a conveying sheath in one implementation mode of the present invention.
Figure 22:
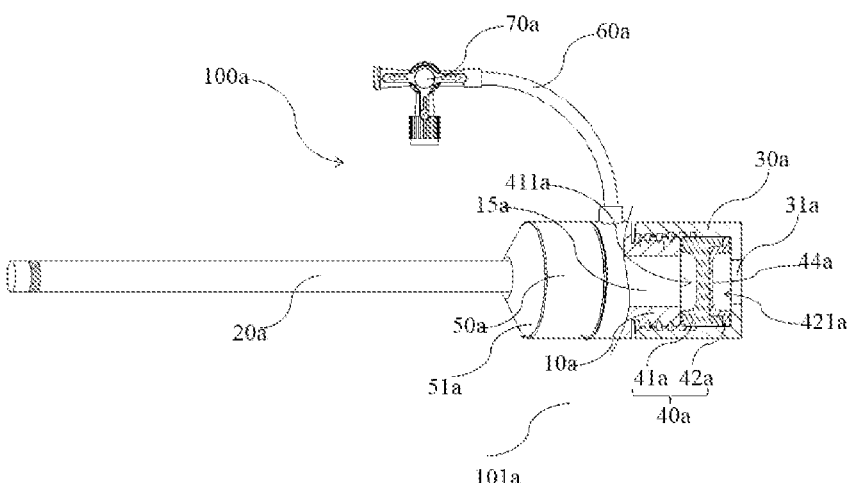
FIG. 22 is a schematic diagram of a partially sectional structure of the conveying sheath in FIG. 21.

One implementation mode of the embodiments provides a conveying sheath 100a. FIG. 21 is a schematic diagram of an exploded structure of a conveying sheath 100a in one implementation mode of the embodiments. FIG. 22 is a schematic diagram of a partially sectional structure of the conveying sheath 100a in FIG. 21. As shown in FIG. 21 and FIG. 22, the conveying sheath 100a in this implementation mode includes a sheath body 20a and a conveying handle 101a, and a proximal end of the sheath body 20a is connected to and communicated with the conveying handle 101a.

In this embodiment, the conveying handle 101a includes a sealing subassembly 40a. A proximal end and a distal end of the sealing subassembly 40a are respectively recessed into the sealing subassembly 40a to form a first cavity 411a and a second cavity 421a. The sealing subassembly 40a internally has a channel 44a that is used for allowing an interventional device to penetrate in and penetrate through. The first cavity 411a, the channel 44a, and the second cavity 421a are communicated so as to penetrate through the proximal end and the distal end of the sealing subassembly 40a. In other embodiments, at least one of the proximal end and the distal end of the sealing subassembly 40a is recessed into the sealing subassembly 40a.

In this embodiment, the maximum inner diameter of the first cavity 411a and the maximum inner diameter of the second cavity 421a are greater than the maximum inner diameter of the channel 44a. It should be noted that the first cavity 411a, the second cavity 421a, and the channel may be cylindrical or of other irregular shapes. If they are of an irregular shape, the maximum inner diameter refers to a maximum length in a direction perpendicular to a conveying direction. The channel 44a with a relatively small maximum inner diameter can be used for allowing the interventional device to pass through, so as to avoid such a phenomenon that if the inner diameter is relatively large, blood leakage will be caused in the process of threading the interventional device in or out. The first cavity 411a and the second cavity 421a have the relatively large maximum inner diameters, so that they can provide a relatively large deformation space.

The conveying handle 101a further includes a connection seat 10a and a rear end cover 30a; a first connection channel 15a is arranged in the connection seat 10a; and the connection seat 10a is further provided with an exhaust port 14a communicated with the first connection channel 15a. The sheath body 20a is arranged at one end of the connection seat 10a and is communicated with the first connection channel 15a; the rear end cover 30a is provided with a second connection channel 31a; the rear end cover 30a is arranged at the other end of the connection seat 10a; a mounting cavity is further included between the rear end cover 30a and the connection seat 10a; the sealing subassembly 40a is arranged in the mounting cavity; and a peripheral surface of the sealing subassembly 40a is in close fit and hermetically connected with an inner wall surface of the mounting cavity. The sealing subassembly 40a is provided with a channel that communicates the first connection channel 15a with the second connection channel 31a. The first cavity 411a is arranged at a position close to the first connection channel 15a, and the second cavity 421a is arranged at a position close to the second connection channel 31a. In other embodiments, the sealing subassembly 40a can ensure the airtightness of the conveying handle 101a as long as the sealing subassembly 40a can be arranged in the conveying handle 101a. Other structures in the conveying handle may be set according to different needs.

According to the conveying sheath 100a in the embodiments, the sealing subassembly 40a is arranged between the connection seat 10a and the rear end cover 30a; the sealing subassembly 40a is provided with the channel 44a used for communicating the first connection channel 15a with the second connection channel 31a; the first cavity 411a is arranged at the position close to the first connection channel 15a; and the second cavity 421a is arranged at the position close to the second connection channel 31a. When the interventional device is inserted into the first connection channel 15a and the sheath body 20a through the second connection channel 31a, the sealing subassembly 40a deforms towards the first connection channel 15a under the action of an impact force of the interventional device; the set first cavity 411a is a deformation space, so that a portion of the interventional device that is in contact with the sealing subassembly deforms in the deformation space. Furthermore, the first cavity 411a is a cavity structure, which can disperse the impact force to effectively reduce the deformation of the entire sealing subassembly 40a, thus maintaining the airtightness of the sealing subassembly 40 and the mounting cavity and reducing the phenomenon of hemorrhage caused by poor sealing effect of the sealing subassembly 40. When the interventional device is pulled out of the sheath body 20a, the sealing subassembly 40a deforms towards the second connection channel 31a under the action of the impact force of the interventional device. The provided second cavity 421a is a deformation space, so that the portion of the interventional device that is in contact with the sealing subassembly deforms in the deformation space. Furthermore, the first cavity 411a is a cavity structure, which can disperse the impact force to reduce the deformation of the sealing subassembly 40a, so as to maintain the airtightness of the sealing subassembly 40a and the mounting cavity and reduce the phenomenon of hemorrhage caused by poor sealing effect of the sealing subassembly 40 in the process of pulling out the device. Therefore, by using the conveying sheath 100a in the embodiments, the sealing effect in the process of establishing an access for the interventional device by the conveying sheath 100a can be effectively ensured; the phenomenon of blood leakage is prevented; the convenience and reliability in the clinical operation process are improved; the surgical risk is lowered; and the safety of clinical operations is improved.

As shown in FIG. 21 and FIG. 22, in some implementation modes of the embodiments, the connection seat 10a includes a connection seat body 11a, and a first connection end 12a and a second connection end 13a respectively arranged at two ends of the connection seat body 11a. In order to ensure the airtightness of connection between the sheath body 20a and the first connection channel 15a, in some implementation modes of the embodiments, the conveying sheath 100a further includes a front end cover 50a. A peripheral surface of the first connection end 12a is provided with an external thread; and an internal thread capable of being matched with the peripheral surface of the first connection end 12a is arranged inside the front end cover 50a.

The proximal end of the sheath body 20a is fixed between the first connection end 12a and the front end cover 50a, and a tube cavity in the sheath body 20a is communicated with the first connection channel 15a. In FIG. 21, the proximal end of the sheath body 20a includes a horn mouth 21a. The way that the proximal end of the sheath body 20a is threaded into the front end cover 50a is that the distal end of the sheath body 20a is threaded in from the proximal end of the front end cover 50a till the horn mouth 21a resists against an opening of the front end cover 50a. The horn mouth 21a is fixed between the front end cover 50a and the first connection end 12a, and the front end cover 50a is in thread fit with the first connection end 12a. In order to ensure the coaxiality between the first connection channel 12a and the tube cavity of the sheath body 20a, the distal end of the front end cover 50a is provided with a mounting slope 51a used for positioning the horn mouth 21a at the proximal end of the sheath body 20a, thereby ensuring the coaxiality between the sheath body 20a and the first connection channel 15a and ensuring that penetration of other interventional devices is successfully. In other implementation modes of the embodiments, the proximal end of the sheath body 20a may also be directly inserted into the first connection channel 15a, or the sheath body 20a and the first connection end 12a are connected in other ways. A specific connection way is not limited, so that it can be ensured that the tube cavity of the sheath body 20 and the first connection channel 15a are communicated to guarantee the airtightness.

A peripheral surface of the second connection end 13a of the connection seat 10a is also provided with an external thread, and an internal thread matched with the peripheral surface of the second connection end 13a is arranged inside the rear end cover 30a; and similarly, the second connection end 13a and the rear end cover 30a are connected through thread fit. After the second connection end 13a and the rear end cover 30a are connected, a mounting cavity for mounting the sealing subassembly 40a is formed between the second connection end 13a and the rear end cover 30a. The peripheral surface of the sealing subassembly 40a is hermetically connected to an inner wall surface of the mounting cavity, thus ensuring the airtightness of the conveying sheath 20a and preventing blood from flowing out of a gap between the peripheral surface of the sealing subassembly 40a and the inner wall surface of the mounting cavity. In the use process of the conveying sheath 100a, an end cover located at the proximal end of the conveying sheath 100a is the rear end cover 30a, and an end cover located at the distal end of the conveying sheath 100a is the front end cover 50a.

An exhaust port 14a is arranged on the connection seat body 11a; the exhaust port 14a is communicated with the first connection channel 15a, so that air in the conveying sheath 100a can be exhausted through the exhaust port 14a in the process that other interventional devices are inserted into and pulled out of the conveying sheath 100a, which prevents the air from entering the blood of the patient in a treatment process and ensures normal flowing of the blood.

In the process of establishing an access by the conveying sheath 100a for an interventional device such as a spring ring, an occluder, a filter, and a stent in an operation, the interventional device is inserted into the conveying sheath 100a from the proximal end of the conveying sheath 100a, i.e., one side of the rear end cover 30a, and other interventional devices pass through the second connection channel 31a, the sealing subassembly 40a, the first connection channel 15a, and the sheath body 20a in sequence to a lesion site.

In some implementation modes of the embodiments, the conveying sheath 100a further includes a connection tube 60a and a three-way valve 70a. One end of the connection tube 60a is communicated with the exhaust port 14a, and the other end of the connection tube 60a is communicated with the three-way valve 70a, so that the air in the conveying sheath 100a can be effectively exported through the connection tube 60a and the three-way valve 70a. Preferably, the connection tube 60a is a hose, such as a rubber tube, which is convenient for adjusting the placement position of the three-way valve 70a.

Figure 23:
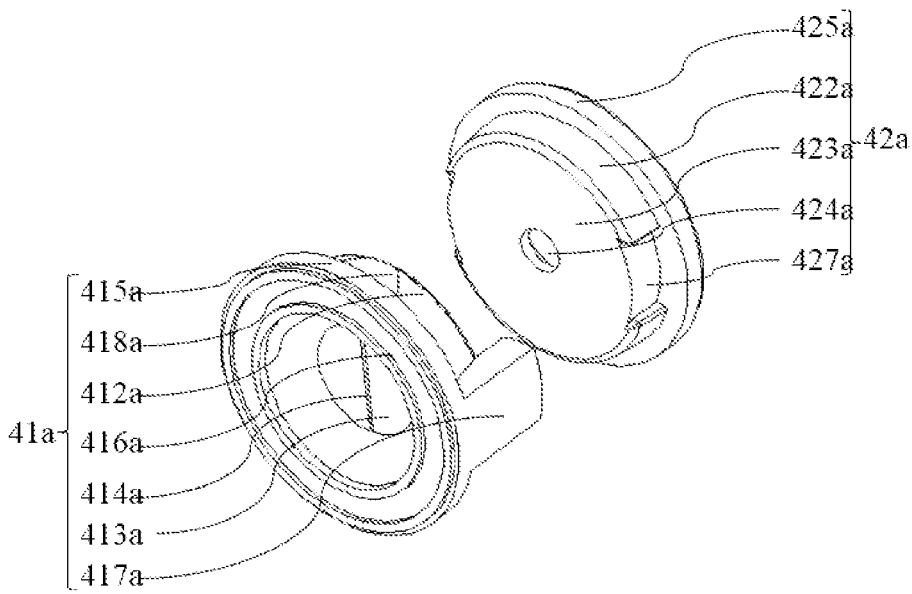
FIG. 23 is a schematic structural diagram of a sealing subassembly in FIG. 21.
Figure 24:
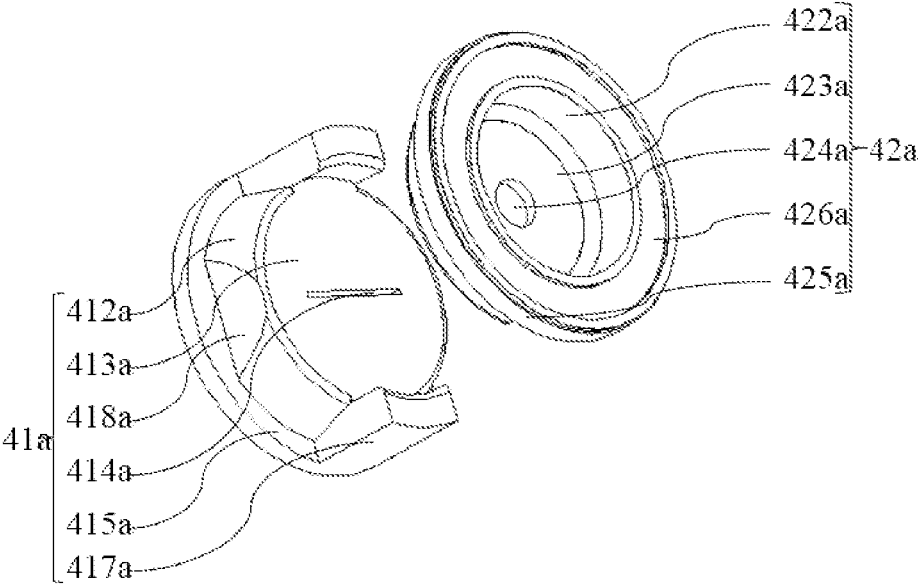
FIG. 24 is a schematic structural diagram of another view of the sealing subassembly in FIG. 23.

FIG. 23 is a schematic structural diagram of a sealing subassembly 40a in FIG. 21. FIG. 24 is a schematic structural diagram of another view of the sealing subassembly 40 in FIG. 23. As shown in FIG. 23 and FIG. 24, in some implementation modes of the embodiments, the sealing subassembly 40a includes a first sealing member 41a and a second sealing member 42a. The first sealing member 41a is provided with the first cavity 411a (referring to FIG. 22), and the first sealing member 41a is further provided with a first through hole 414a that penetrates through the first cavity 411a. The second sealing member 42a is provided with the second cavity 421a (referring to FIG. 22), and the second sealing member 42a is further provided with a second through hole 424a that penetrates through the second cavity. The first through hole 414a and the second through hole 424a are communicated, thus forming the channel 44a (referring to FIG. 22). In other embodiments, the sealing subassembly 40a may be of an entire structure. In other embodiments, only one of the first sealing member 41a and the second sealing member 42a has a cavity structure.

By the arrangement of the first cavity 411a and the second cavity 421a, it can be effectively ensured that there is a cavity serving as a deformation space in the process that an interventional device is inserted into and pulled out of the conveying sheath 100a. A portion of the interventional device that is in contact with the sealing subassembly (for example a portion near the first through hole 414a and the second through hole 424a) to deform in the deformation space. Furthermore, the cavity structure can disperse the impact force, which can effectively reduce the deformation of the sealing subassembly 40a with respect to the conveying handle and ensure the sealing effect inside the conveying sheath 100a. In order to ensure that the first sealing member 41a and the second sealing member 42a have certain deformability, the first sealing member 41a and the second sealing member 42a may select a material such as silica gel or silicone resin that has certain recoverability.

The first sealing member 41a and the second sealing member 42a may be set to have a same elastic modulus or different elastic moduli. If the value of the elastic modulus is greater, a seal is harder, and it is more difficult to cause deformation. The elastic modulus of the first sealing member 41a may be set to be less than the elastic modulus of the second sealing member 42a, so that a material of the first sealing member 41a is softer, and the passing performance of other interventional devices is higher; and a material of the second sealing member 42a located at the proximal end is harder, and the second sealing member 42a is unlikely to deform to ensure the airtightness.

In some implementation modes of the embodiments, the first sealing member 41a includes a first circumferential part 412a and a first bottom plate part 413a. The first bottom plate part 413a is arranged on an end surface of the first circumferential part 412a facing the second sealing member 42a; the first bottom plate part 413a is provided with the first through hole 414a; and the first circumferential part 412a and the first bottom plate part 413a are jointly encircled to form the first cavity 411a (referring to FIG. 22). The second sealing member 42a includes a second circumferential part 422a and a second bottom plate part 423a. The second bottom plate part 423a is arranged on an end surface of the second circumferential part 422a facing the first sealing member 41a; the second bottom plate part 423a is provided with the second through hole 424a; and the second circumferential part 422a and the second bottom plate part 423a are jointly encircled to form the second cavity 421a (referring to FIG. 22).

As shown in FIG. 23 and FIG. 24, the first cavity 411a of the first sealing member 41a and the second cavity 421a of the second sealing member 42a are of bowl-shaped structures. One end of each bowl-shaped structure is provided with an opening, and the first bottom plate part 413a and the second bottom plate part 423a are fitted to each other.

In the process that an interventional device is inserted into the conveying sheath 100a, the first bottom plate part 413a and the second base plate part 423a deform towards the first cavity 411a. Since the cavity structure of the first cavity 411a can provide a deformation space for the first bottom plate part 413a and the second base plate part 423a and can disperse the impact force, which can greatly reduce the impact force transmitted to the first circumferential part 412a and the second circumferential part 422a, can avoid a movement of the entire sealing subassembly in the mounting cavity with respect to the conveying handle, and can improve the airtightness, thus reducing the phenomenon of blood leakage.

In the process that other interventional devices are inserted into the conveying sheath 100a, the first bottom plate part 413a and the second base plate part 423a deform towards the second cavity 421a. Since the cavity structure of the second cavity 421a can provide a deformation space for the first bottom plate part 413a and the second base plate part 423a and can disperse the impact force, which can greatly reduce the impact force transmitted to the first circumferential part 412a and the second circumferential part 422a, can avoid a movement of the entire sealing subassembly in the mounting cavity with respect to the conveying handle, and can improve the airtightness, thus reducing the phenomenon of blood leakage.

Since the first bottom plate part 413a and the second bottom plate part 423a are fitted to each other, when the second bottom plate part 423a deforms towards the first cavity 411a, the first bottom plate part 413a can also counteract one part of an acting force of the second bottom plate part 423a towards the first cavity 411a under the action of the impact force of the interventional device; or when the first bottom plate part 413a deforms towards the second cavity 421a, the second bottom plate part 423a can also counteract one part of an acting force of the first bottom plate part 413a towards the second cavity 421a under the action of the impact force of the interventional device.

In other implementation modes of the embodiments, the first through hole 414a on the first bottom plate part 413a is "⌒"-shaped, and the second through hole 424a on the second bottom plate part 423a is round. When a sheath core, a guide wire or other interventional devices pass through the sealing subassembly 40a, the round through hole on the second bottom plate part 423a may tightly wrap a guide tube, the guide wire, or other devices, thereby effectively preventing the phenomenon of blood leakage; at the same time, the "⌒"-shaped through hole on the first bottom plate part 413 can provide good passing performance for the sheath core, the guide wire, or other interventional devices and makes a certain activity space. When the sheath core, the guide wire or other devices are pulled out of the conveying sheath 100a, the second sealing member 42a fitted to the first sealing member 41a may provide a good support force for the first sealing member 41a, which is conductive to closing the "⌒"-shaped through hole of the first sealing member 41a and achieving a good sealing effect. When there is little blood oozes out, the second sealing member 42a can also provide a second barrier for the little blood, which further reduces the phenomenon of blood leakage. The shapes of the first through hole 414a and the second through hole 424a are not limited this. In other implementation modes of the embodiments, the first through hole 414a and the second through hole 424a can also be a cross through hole and a *-shaped through hole.

In other implementation modes of the embodiments, one of the first sealing member 41a and the second sealing member 42a may also be set to be a structural form, two ends of which are provided with bottom plate parts. Corresponding through holes for allowing other interventional devices to pass are formed in the bottom plate parts. Alternatively, the first sealing member 41a and the second sealing member 42a are both set to be structural forms, two ends of which are provided with bottom plate parts, and corresponding through holes for allowing other interventional devices to pass are formed in the bottom plate parts. All the above structural forms can achieve the purpose of solving the problems in the embodiments.

In some implementation modes of the embodiments, the first sealing member 41a further includes a first boss 415a. The first boss 415a is arranged on the end surface of the first circumferential part 412a facing the first connection channel 15a and protrudes from an outer side wall of the first circumferential part 412a. The second sealing member 42a further includes a second boss 425a. The second boss 425a is arranged on the end surface of the second circumferential part 422a facing the second connection channel 31a and protrudes from an outer side wall of the second circumferential part 422a.

In some implementation modes of the embodiments, the first sealing member 41a and the second sealing member 42a are matched with the inner wall surface of the mounting cavity through the bosses, thereby achieving the sealing effect of the sealing subassembly 40a. Since the first boss 415a and the second boss 425a protrude from the respective corresponding circumferential parts, in the matching process of the sealing subassembly 40*a* and the mounting cavity, only the first boss 415*a* and the second boss 425*a* deform under an extrusion force, but the first bottom plate part 413*a* and the second bottom plate part 423*a* will not deform, and the first through hole 414*a* and the second through hole 423*a* are not caused to deform, thereby ensuring that the interventional device can be successfully inserted into and pulled out of the sealing subassembly 40*a*. In other embodiments, the first boss 415*a* may be flush with the outer side wall of the first circumferential part 412*a*, and the second boss 425 may be flush with the outer side wall of the second circumferential part 422*a*.

In some implementation modes of the embodiments, a first groove 416*a* is further arranged on an end surface of the first boss 415*a*, and a second groove 426*a* is further arranged on an end surface of the second boss 425*a*. In the process of connecting the rear end cover 30*a* with the second connection end 13*a*, the end surface of the first boss 415*a* is fitted to the second connection end 13*a*, and the end surface of the second boss 425*a* is fitted to the rear end cover 30*a*; the sealing subassembly 40*a* is extruded by the rear end cover 30*a* and the second connection end 13*a* to deform, so as to exhaust air in the first groove 416*a* and the second groove 426*a*, which enables the first boss 415*a* and the second boss 425*a* to generate suction forces with the respective corresponding end surfaces; the first groove 416*a* and the second groove 426*a* respectively form sealing rings on the respective corresponding end surfaces, thus further ensuring the sealing effect between the peripheral surface of the sealing subassembly 40*a* and the inner wall surface of the mounting cavity. In other embodiments, grooves may also be arranged on side surfaces of the first boss 415*a* and the second boss 425*a*.

In this embodiment, when the first boss 415*a* and the second boss 425*a* are ring bosses, the first groove 416*a* and the second groove 426*a* are also ring grooves. In other embodiments, at least one of the first boss 415*a* and the second boss 425*a* includes a plurality of convex blocks. The plurality of convex blocks are distributed at peripheries of the circumferential parts. Grooves may be formed between the plurality of convex blocks.

In some implementation modes of the embodiments, a first fixing part 417*a* is arranged on the first sealing member 41*a*, and a second fixing part 427*a* matched with the first fixing part 417*a* is arranged on the second sealing member 42*a*. For example, as shown in FIG. 23 and FIG. 24, the first fixing part 417*a* is an extending end that is arranged on the peripheral surface of the first circumferential part 412*a* and faces the second sealing member 42*a*; the second fixing part 427*a* is a groove arranged on the peripheral surface of the second circumferential part 422*a*. The extending end can be inserted into the groove in a shape matching manner so as to connect and fix the first sealing member 41*a* with the second sealing member 42*a*, which causes the first bottom plate part 413*a* and the second base plate part 423*a* to be in close fit, achieves axial and circumferential positioning of the first sealing member 41*a* and the second sealing member 42*a*, and effectively prevents the first sealing member 41*a* and the second sealing member 42*a* from moving. In addition, the first fixing part 417*a* may also be a groove, and the second fixing part 427*a* is an extending end matched with the groove in shape.

In some implementation modes of the embodiments, a cut 418*a* is also arranged on the peripheral surface of the first circumferential part 412*a*, so that after the first boss 415*a* is extruded to deform, there is an enough deformation space, which prevents further extrusion to the first circumferential part 412*a* and ensures that the hole diameter of the first through hole 414*a* is not changed. Correspondingly, a cut may also be arranged on the peripheral surface of the second circumferential part 422*a*.

The invention claimed is:

1. A sheath, comprising: a sheath body, a handle, and a traction wire, a proximal end of the sheath body being connected to the handle, and the traction wire being connected to the sheath body and the handle, wherein the traction wire comprises a first traction wire; the handle comprises a first guide rail member and a first slider; the first slider is connected to the first traction wire; a first groove is provided on an outer wall of the first guide rail member along an axial direction; the first groove comprises a first bottom and a first side wall; the first slider slides in the first groove along the first side wall to drive the first traction wire to move, wherein at least part of the outer wall of the first guide rail member is radially recessed to a center axis of the first guide rail member to form the first groove; or the first bottom of the first groove is at least part of an outer surface of the first guide rail member, and the first side wall is located on the outer surface of the first guide rail member;

wherein a first fixing ring is arranged in the sheath body; the first fixing ring has a side wall comprising an outer surface and an inner surface in a radial direction;

the side wall of the first fixing ring is provided with a first hole, a second hole, and a third hole; the first hole, the second hole and the third hole all penetrate through the outer surface and the inner surface; the second hole is closer to a distal end of the first fixing ring than the first hole and the third hole; a first connecting line is reserved between a center of the first hole and a center of the second hole, and a second connecting line is reserved between a center of the third hole and the center of the second hole; an obtuse angle is set between the first connecting line and the second connecting line; the proximal end of the first traction wire is connected to the first slider; and the distal end of the first traction wire passes through the first hole, the second hole, and the third hole in sequence or passes through the third hole, the second hole, and the first hole in sequence, then extends towards the proximal end, and is connected to the first slider again.

2. The sheath according to claim 1, wherein a slideway is arranged in the first groove, and the first slider slides on the slideway.

3. The sheath according to claim 1, wherein the handle further comprises a housing and a first gyration subassembly; the first gyration subassembly is rotatably connected to the housing; the first slider is arranged in the first gyration subassembly; and an inner wall of the first gyration subassembly is in threaded connection with the first slider.

4. The sheath according to claim 3, wherein a distal end or proximal end of the first guide rail member is provided with a catch structure which is clamped and abutted with the housing.

5. The sheath according to claim 1, wherein the first guide rail member has a tube cavity structure, and the proximal end of the sheath body is threaded out of a proximal end of the tube cavity structure via the tube cavity structure;

a proximal end of the first traction wire is threaded out of a wall of the sheath body, enters the first groove, and is connected to the first slider; or the first guide rail member has a first opening; the proximal end of the first traction wire enters the first groove via the first opening and is connected to the first slider.

6. The sheath according to claim 1, wherein the handle further comprises a support member; the first guide rail member has a tube cavity structure; at least part of the support member is arranged in the tube cavity structure of the first guide rail member; and the sheath body passes through the support member and is collected in the support member.

7. The sheath according to claim 6, wherein the support member comprises a first catch part and a first collecting part; the first catch part and the first collecting part are axially connected, or the first collecting part axially penetrates through the first catch part, wherein an outer diameter of the first catch part is greater than an inner diameter of the tube cavity structure of the first guide rail member, and the first catch part resists against a proximal end surface or a distal end surface of the first guide rail member; and at least part of the first collecting part is arranged in the tube cavity structure of the first guide rail member; the at least part of the first collecting part that is arranged in the tube cavity structure of the first guide rail member and at least part of an inner surface of the tube cavity structure of the first guide rail member are encircled to form a channel space; the channel space is communicated with the tube cavity structure of the first guide rail member; an axial center axis of the channel space is parallel to or coaxial with the center axis of the first guide rail member; and the sheath body passes through the first collecting part and is collected in the first collecting part.

8. The sheath according to claim 1, wherein the first guide rail member comprises a stopper which is arranged in the first groove to restrain a sliding length of the first slider.

\* \* \* \* \*